United States Patent [19]

Graziella

[11] Patent Number: 5,362,745
[45] Date of Patent: Nov. 8, 1994

[54] ORAL PHARMACEUTICAL COMPOSITIONS CONTAINING MELATONIN

[75] Inventor: Bruno Graziella, Milan, Italy
[73] Assignee: Medea Research S.r.l., Milan, Italy
[21] Appl. No.: 969,181
[22] PCT Filed: Aug. 7, 1991
[86] PCT No.: PCT/EP91/01486
  § 371 Date: Feb. 4, 1993
  § 102(e) Date: Feb. 4, 1993
[87] PCT Pub. No.: WO92/02207
  PCT Pub. Date: Feb. 20, 1992

[30] Foreign Application Priority Data
  Aug. 10, 1990 [IT] Italy ............ 21263 A/90

[51] Int. Cl.⁵ .............. A61K 31/21; A61K 31/275
[52] U.S. Cl. ....................... 514/415; 514/419
[58] Field of Search .............. 514/415, 419, 78

[56] References Cited

U.S. PATENT DOCUMENTS 4,388,324 6/1983 Horrobin ............... 514/474
4,746,674 5/1988 Pierpaoli et al. ....... 514/415
4,855,305 8/1989 Cohen .................... 514/171

OTHER PUBLICATIONS

Merck Index, Eleventh Edition (1989) #5311.

Primary Examiner—Marianne M. Cintins
Assistant Examiner—T. J. Criares
Attorney, Agent, or Firm—Bucknam and Archer

[57] ABSTRACT

Oral pharmaceutical compositions containing melatonin as the active principle in form of micro-emulsion are described.

4 Claims, No Drawings

ORAL PHARMACEUTICAL COMPOSITIONS CONTAINING MELATONIN

The present invention refers to oral pharmaceutical compositions containing melatonin.

Melatonin an hormone synthesized in the epiphysis, in the retina and, presumably in the chromaffinic cells of the intestinal tract. Its biosynthesis is subjected to a typical circadian rhythm, reaching a peak during the night. Its effects are numerous and particular attention has been recently focused on the immunostimulant and immunomodulatory effect of melatonin. A problem which considerably limits the therapeutic potentials of this hormone is however provided by its poor oral bioavailability.

It has now been found that melatonin may be effectively admininistered by the oral route when formulated in form of micro-emulsions.

Micro-emulsions are well-known and may be prepared according to conventional methods: a review of their properties and preparative methods has been recently published on Chemistry in Britain Vol. 26 (4) April 1990, 342-344 and cited references.

As a pharmaceutically acceptable emulsifier, lecithins or purified components thereof such as L-α-phosphatidylcholine, L-α-phosphatidylethanolamine or L-α-phosphatidylserine, both extractive and synthetic, are preferred. L-α-phosphatidylcholine is preferably used in a weight ratio to melatonin of about 1:1 in a solution consisting of ethanol, propylene glycol and water.

The active principle and a thicken agent such as gelatine, natural gums, cellulose derivatives and the like are then added to the above solution obtained by usual methods.

The following example further illustrate the invention.

EXAMPLE

Formulations in micro-emulsions 1.2 g of L-α-phosphatidylcholine are dispersed under vigorous agitations in 4.8 ml of a solution consisting of [ethanol(2)/propylene glycol (1)]/H$_2$O=55/45 pp.

After emulsifying, 1.5 g of melatonin are added, under stirring and then, after complete dissolution, 1 g of gelatine.

The so obtained micro-emulsion, hereinafter referred to as MR-111, has been subjected to pharmacokinetics studies, evaluating the serum levels of melatonin in healthy volunteers, according to the following method.

Experimental part

Two healthy volunteers were treated at the zero (0) time with a dose of 2.5 mg, respectively of melatonin (subject 1) and of MR-111 (subject 2).

5 ml of venous blood were sampled at the times, expressed in minutes, 0, 30, 90, 150, 210, 270 and 330.

After separation, serum was frozen till the melatonin extraction. The extraction and the determination of melatonin were carried out according to the methods of Maestroni et al., J. Neuroimmunol. 13, 19-30, 1986.

Results
Serum levels of melatonin expressed in pg/ml.

| Time (minutes) | Melatonin | MR-111 |
| --- | --- | --- |
| 0 | 25 | 27 |
| 30 | 362 | 268 |
| 90 | 1788 | 719 |
| 150 | 240 | 984 |
| 210 | 680 | 844 |
| 270 | 66 | 439 |
| 330 | 0 | 295 |
| 390 | 0 | 199 |
| 405 | 0 | 93 |

The administration of 2.5 mg of melatonin (subject 1) confirms the kinetics observed in other studies (Wright J. et al., Clin. Endocrinol., 24, 375-382(1989); Lieberman H. R. J. Neural. Trans., 21, 233-24 (Suppl.) (1986) with an high peak after 90 minutes and a fast decrease of the plasma concentration.

The product MR-111 induces a wider peak, more similar to the physiological peak of melatonin, surprisingly showing a higher bioavailability.

I claim:

1. An oral pharmaceutical composition consisting of melatonin as the active principle in form of a micro-emulsion, L-α-phosphatidylcholine as an emulsifier and a solvent mixture consisting of ethanol, propylene glycol and water and wherein the weight ratio of L-α-phosphatidylcholine to melatonin is about 1:1 and wherein the composition optionally contins a thicker agent.

2. The composition according to claim 1 which contains at least one thickening agent selected from the group consisting of gelatin, natural gums and cellulose derivatives.

3. The composition according to claim 3 wherein the thickening agent is gelatin.

4. A method of increasing the bioavailability of melatonin by oral administration to a human subject which consists of administering to said subject a microemulsion consisting of melatonin, L-α-phosphatidylcholine as the emulsifier and a solvent mixture consisting of ethanol, propylene glycol and water and wherein the weight ratio of L-α-phosphatidylcholine to melatonin is about 1:1.

* * * * *